(12) United States Patent
Claus et al.

(10) Patent No.: US 7,103,136 B2
(45) Date of Patent: Sep. 5, 2006

(54) FLUOROSCOPIC TOMOSYNTHESIS SYSTEM AND METHOD

(75) Inventors: Bernhard Erich Hermann Claus, Niskayuna, NY (US); Jeffrey Wayne Eberhard, Albany, NY (US); David Allen Langan, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 195 days.

(21) Appl. No.: 10/745,315

(22) Filed: Dec. 22, 2003

(65) Prior Publication Data

US 2005/0135558 A1    Jun. 23, 2005

(51) Int. Cl.
*A61B 6/03* (2006.01)
(52) U.S. Cl. .............................. 378/4; 378/22
(58) Field of Classification Search .............. 378/4, 378/15, 22, 62
See application file for complete search history.

(56) References Cited

U.S. PATENT DOCUMENTS

| | | | |
|---|---|---|---|
| 5,175,754 A * | 12/1992 | Casey et al. ................... 378/4 |
| 5,530,935 A * | 6/1996 | Dillen ......................... 378/98.2 |
| 6,196,715 B1 * | 3/2001 | Nambu et al. ............... 378/197 |
| 6,396,898 B1 * | 5/2002 | Saito et al. .................... 378/19 |
| 6,666,579 B1 * | 12/2003 | Jensen ......................... 378/197 |
| 6,760,404 B1 * | 7/2004 | Saito et al. ................. 378/98.8 |
| 6,895,077 B1 * | 5/2005 | Karellas et al. ............ 378/98.3 |
| 2002/0085681 A1 * | 7/2002 | Jensen ......................... 378/197 |
| 2003/0169847 A1 * | 9/2003 | Karellas et al. ............ 378/98.3 |
| 2003/0220555 A1 * | 11/2003 | Heigl et al. ................. 600/407 |
| 2005/0053200 A1 * | 3/2005 | Sukovic et al. ............. 378/210 |
| 2005/0054916 A1 * | 3/2005 | Mostafavi ................... 600/427 |

\* cited by examiner

*Primary Examiner*—Edward J. Glick
*Assistant Examiner*—Chih-Cheng Glen Kao
(74) *Attorney, Agent, or Firm*—Fletcher Yoder

(57) ABSTRACT

A technique is provided for generating a three-dimensional image from fluoroscopic projection images. The technique allows for the acquisition of fluoroscopic images at different perspectives relative to a region of interest. One or more three-dimensional images may then be reconstructed from the fluoroscopic projection images. The three-dimensional images may then be displayed to provide anatomic context for the fluoroscopic application. A fluoroscopic projection image, such as the most current fluoroscopic image, may be superimposed on the three-dimensional image if desired.

56 Claims, 1 Drawing Sheet

FLUOROSCOPIC TOMOSYNTHESIS SYSTEM AND METHOD

BACKGROUND OF THE INVENTION

The present invention relates generally to the field of medical imaging, and more specifically to the field of x-ray fluoroscopy. In particular, the present invention relates to the generation of three-dimensional data from fluorscopic image sequences.

In the field of medical imaging, fluoroscopy is a technique for generating real-time X-ray, low-dose image sequences. Because of this real-time aspect, fluoroscopy is useful for visualizing motion or processes that develop over time. For example, fluoroscopy may be employed intraoperatively, i.e., during surgical interventions or invasive procedures, such as to facilitate insertion or movement of catheters or other devices or to facilitate bone repair. In addition, fluoroscopy may be used in angiography, gastrointestinal tract imaging, and urography, to provide real-time imaging of the flow patterns of contrast-enhanced bodily fluids. The frame rate of the sequence of images may range from a few frames per second (fps) to 60 fps or more, depending on the application. For instance, cardiac angiography, where the anatomy is normally in rapid motion, would typically be performed at a high frame rate.

Fluoroscopic imaging is limited in some respects, however. For example, as with other forms of X-ray projection imaging, fluoroscopic images are two-dimensional representations of three-dimensional anatomic regions. As a result, overlying anatomical structures may make image interpretation more difficult. In addition, the anatomical context of the fluoroscopic images may be difficult to ascertain without a three-dimensional references. In addition, due to the low dose typically associated with fluoroscopic imaging, the images may be relatively noisy. Aspects of the present technique may address one or more of the problems set forth above.

BRIEF DESCRIPTION OF THE INVENTION

The present technique provides a novel approach to fluoroscopic imaging. In particular, the present technique provides for the acquisition of fluoroscopic projection images at a variety of perspectives relative to a region of interest. The projection images acquired at the various perspectives may be utilized to reconstruct a three-dimensional image of the region which, when displayed, provides a three-dimensional anatomic context for the region of interest. The three-dimensional image may be continuously updated or regenerated to incorporate newly acquired fluoroscopic projection images. A current fluoroscopic image may be superimposed on the three-dimensional image, if desired, for display, allowing an operator to view the most recent fluoroscopic image in a three-dimensional anatomic context.

In accordance with one aspect of the technique, a method is provided for generating a three-dimensional image. In accordance with this aspect, two or more fluoroscopic projection images are acquired at different view angles relative to a region of interest. At least one three-dimensional image may be reconstructed from the two or more fluoroscopic projection images. Systems and computer programs that afford functionality of the type defined by these aspects are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
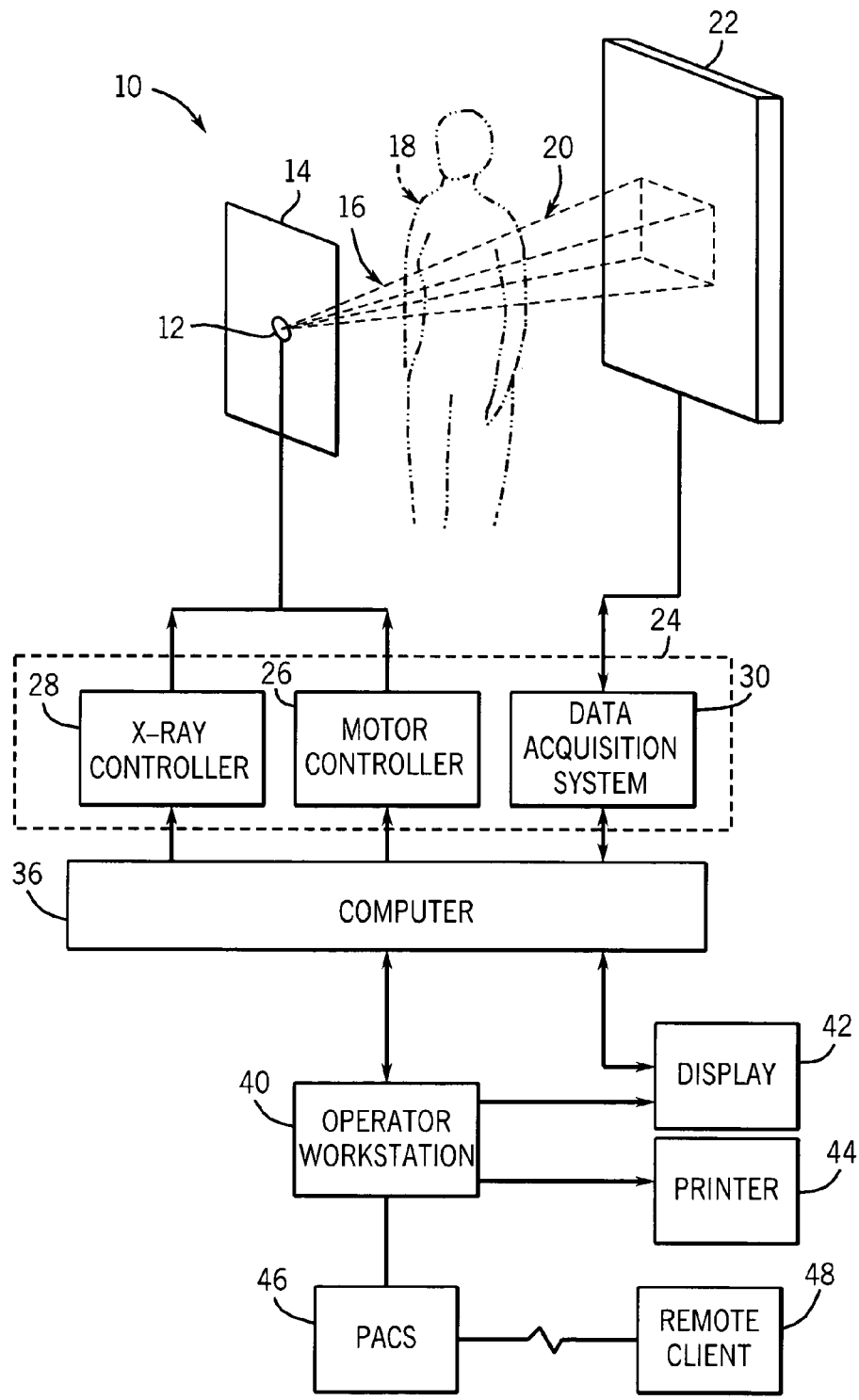
FIG. 1 is a diagrammatical view of an exemplary imaging system suitable for acquiring fluoroscopic images in accordance with aspects of the present technique.

In the field of medical imaging, various imaging modalities may be employed to non-invasively examine and/or diagnose internal structures of a patient using various physical properties. One such modality is x-ray fluoroscopic imaging, which acquires a real-time, low-dose image sequence useful for viewing motion and/or events that occur over time. Fluoroscopic images, however, may suffer from those shortcomings common to other X-ray projection imaging techniques. The present technique addresses one or more of these problems. In particular, the present technique allows, among other things, for the generation of a three-dimensional context for fluoroscopic images from the fluoroscopic image sequence.

An example of an X-ray imaging system 10 capable of acquiring and/or processing fluoroscopic image data in accordance with the present technique is illustrated diagrammatically in FIG. 1. As depicted, the imaging system 10 includes an X-ray source 12, such as an X-ray tube and associated support and filtering components. The X-ray source 12 may be affixed to a support, such a C-arm, fluoroscope stand, or examination table, which allows the X-ray source 12 to be moved within a constrained region. As one of ordinary skill in the art will appreciate, the constrained region may be arcuate or otherwise three-dimensional, depending on the nature of the support. For simplicity, however, the constrained region is depicted and discussed herein as a plane 14 within which the source 12 may move in two-dimensions. A collimator may also be present, which defines the size and shape of the X-ray beam 16 that emerges from the X-ray source 12.

A stream of radiation 16 is emitted by the source 12 and passes into a region in which a subject, such as a human patient 18, is positioned. A portion of the radiation 20 passes through or around the subject and impacts a detector, represented generally at reference numeral 22. In practice, the detector 22 may be an image intensifier that transforms the spatial patterns of X-ray photons emerging from the patient 18 into an optical image. For real time viewing, this optical image may be acquired by a video camera or a charge coupled device (CCD). Alternately, the detector 22 may comprise detector array, such as a standard flat-panel detector having high detector quantum efficiency (DQE), low noise, and/or fast read-out times. In such an implementation, the detector 22 may be formed by a plurality of detector elements, generally corresponding to pixels, which produce electrical signals that represent the intensity of the incident X-rays. These signals are acquired and processed to reconstruct an image of the features within the subject in real-time or near real-time. An X-ray absorbing shield with an opening for the stream of radiation 16, 20 may be positioned to reduce the scatter, such as in the direction of a clinician. The X-ray shield may be positioned anywhere between the stream of radiation 16 and the clinician and may have a variable lateral extent to allow easy positioning of the x-ray image chain.

Source 12 is controlled by a system controller 24 which furnishes both power and control signals for fluoroscopic examination sequences, including positioning of the source 12 relative to the patient 18 and the detector 22. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system 10 to execute examination protocols and to acquire the resulting data.

In the exemplary imaging system 10, the system controller 24 commands the movement of the source 12 within the plane 14 via a motor controller 26, which moves the source 12 relative to the patient 18 and the detector 22. In alternative implementations, the motor controller 26 may move the detector 22, or even the patient 18, instead of or in addition to the source 12. Additionally, the system controller 24 may include an X-ray controller 28 to control the activation and operation, including collimation, of the X-ray source 12. In particular, the X-ray controller 28 may be configured to provide power and timing signals to the X-ray source 12. By means of the motor controller 26 and X-ray controller 28, the system controller 24 may facilitate the acquisition of radiographic projections at various angles through the patient 18.

The system controller 24 may also include a data acquisition system 30 in communication with the detector 22. The data acquisition system 30 typically receives data collected by the detector 22, such as sampled analog signals. The data acquisition system 30 may convert the data to digital signals suitable for processing by a processor-based system, such as a computer 36.

The computer 36 is typically coupled to the system controller 24. The data collected by the data acquisition system 30 may be transmitted to the computer 36 for subsequent processing and reconstruction. For example, the data collected from the detector 22 may undergo preprocessing and calibration at the data acquisition system 30 and/or the computer 36 to condition the data to represent the line integrals of the attenuation coefficients of the scanned objects. The processed data, commonly called projections, may then be backprojected to formulate images of the scanned area. Once reconstructed, the images produced by the system of FIG. 1 reveal an internal region of interest of the patient 18 which may be used for diagnosis, evaluation, and so forth.

The computer 36 may comprise or communicate with memory circuitry that can store data processed by the computer 36 or data to be processed by the computer 36. It should be understood that any type of computer accessible memory device capable of storing the desired amount of data and/or code may be utilized by such an exemplary system 10. Moreover, the memory circuitry may comprise one or more memory devices, such as magnetic or optical devices, of similar or different types, which may be local and/or remote to the system 10. The memory circuitry may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 which may be equipped with a keyboard and/or other input devices. An operator may thereby control the system 10 via the operator workstation 40. Thus, the operator may observe reconstructed images and other data relevant to the system from computer 36, initiate imaging, and so forth.

A display 42 coupled to the operator workstation 40 may be utilized to observe the reconstructed images and to control imaging. Additionally, the images may also be printed by a printer 44 that may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 may be coupled to a remote system 48, radiology department information system (RIS), hospital information system (HIS) or to an internal or external network, so that others at different locations may gain access to the image and to the image data.

It should be further noted that the computer 36 and operator workstation 40 may be coupled to other output devices that may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Once reconstructed and combined, the image data generated by the system of FIG. 1 reveals internal features of the patient 18. In particular, the resulting sequence of low-dose images may be viewed in real time to reveal motion or time-dependent information related to anatomy or interventional. As noted previously, however, fluoroscopic images, as with other images acquired using conventional X-ray projection techniques, may fail to provide three-dimensional context that may be useful to the viewer.

The present technique addresses such problems by using fluoroscopic images acquired over some interval, such as over all or part of an examination or procedure, to reconstruct a three-dimensional image of the anatomy of interest in real time. Because fluoroscopic image data may be acquired in near real time, the three-dimensional image may be continuously updated. The three-dimensional image may then be used to provide anatomical context for the current fluoroscopic frame.

For example, the three-dimensional image may be displayed by a volume rendering technique. If desired, the current fluoroscopic frame may be superimposed on the rendered volume superimposed. In addition, the fluoroscopic image sequence alone, i.e., without the underlying three-dimensional context, may be displayed on a second monitor to assure high-resolution viewing and to assure consistency with today's clinical practice. The use of three-dimensional imaging in this manner to remove overlying structure in X-ray projections may provide better visualization of anatomy and may reduce the need for double contrast procedures, such as air and barium injections, in some contexts.

I. Image Acquisition

1. Source and Detector Configurations and Trajectories

During acquisition of the fluoroscopic image data, images of the region of interest may be acquired along a scanning trajectory which positions the source 12 and/or detector 22 at a variety of perspectives or orientations relative to the patient 18 over some interval of time. The scanning trajectory, though most easily conceptualized as the movement of the source, generally defines by the movement of the source 12, patient 18, and detector 22 with respect to one another. In general, the scanning trajectory allows the acquisition of fluoroscopic image data at various view angles, which in turn allows the generation of three-dimensional images.

For example, the X-ray source 12 and/or detector may be moved in a circular or other rotational trajectory about the anatomic region of interest. Furthermore, the trajectory may include motion in one, two, or three dimensions or may keep an arbitrary plane in focus. Similarly, a bi-plane scanning mode may be employed with two imaging chains to allow a wider range of viewing orientations. Indeed, any generalized scanning trajectory or trajectories may be used during acquisition of the input image sequence. Along a trajectory, the source 12 may be activated at various acquisition points corresponding to positions or angles for which image data is desired. Depending on the trajectory and application, the acquisition points may be uniformly or non-uniformly sampled. Furthermore, the acquisition points may be clustered or distributed based on a preferred orientation or orientations or may be those acquisition points associated with common clinical procedures, such as spin, bolus chasing, and so forth.

To accomplish the relative motion described by the scan trajectory, the source 12 may be moved, the detector 22 may be moved, or the source 12 and detector 22 may be moved in synchrony, as might be accomplished if both the source 12 and detector 22 were mechanically connected, such as by a C-arm support. In addition, the patient 18 may be moved in addition to or instead of the source 12 and detector 22.

With regard to configurations in which the source 12 and the detector 22 are mechanically connected, various implementations are possible. In such configurations, the X-ray source 12 may be manually positioned with the detector 22 following the motion, such as may occur using a C-arm support. Such a C-arm configuration, or other mechanical coupling may allow acquisitions along any rotation, translation, or variable SID configuration. For example, using a C-arm configuration, the source 12 and detector 22 may be rotated around the body and along the main axis of the body, acquiring projections that may be combined for better quality three-dimensional images.

Alternatively, a detector 22 not connected to the source 12 may be employed instead of or in addition to a fixed detector 22. Such an independent detector 22 may provide greater positional flexibility and variability. For example, an independent detector 22 may be connected to the imaging system 10 via tether that may provide positional information necessary for image reconstruction.

A tomosynthesis system may also be employed to acquire fluoroscopic image data. For example, a tomosynthesis system may be configured to emit low-dose, fluoroscopic levels of X-rays from an X-ray source 12 to achieve a desired number of frames per second while moving along an arbitrary scan trajectory relative to the patient. A stationary detector 22 may be employed, such as a flat-panel detector. Alternately, as discussed above, the tomosynthesis detector may be configured to move in conjunction with, but essentially opposite of, the x-ray source 12 with respect to the imaged patient along the arbitrary scan trajectory.

As one of ordinary skill in the art will appreciate, accurate positional information regarding the source 12 and detector 22 along the scan trajectory facilitates the alignment of the projections from the various beam orientations. Positional sensors may be employed on one or both of the source 12 and the detector 22, depending on the desired accuracy and the relative motion independence of the source 12 and the detector 22. For example, the positional information may be obtained by an electromagnetic positional mechanism, such as an RF tag or other marked or sensor which may be attached to the source 12 or detector 22. In addition, fiducial markers in the acquired image data may be used to facilitate the alignment of the projections, allowing the accuracy of the mechanical positioner and/or sensors to be relaxed. Similarly, anatomical structures within the acquired image data may be used to facilitate the alignment.

2. Frame Timing and Position

The selection of timing, i.e., frame rate, and position of successive fluoroscopic images may be determined by a variety of factors. In the simplest case, the position and timing may be in accordance with standard clinical practice for the procedure being performed. However, other available information may also be considered.

For example, timing and positioning for successive image acquisition may be modified based upon the existing three-dimensional data. In this example, the positioning of the source 12 may be determined by the image quality of the three-dimensional image. For instance, depth resolution, enhanced suppression of overlying tissue, artifact reduction, signal to noise improvement, acquisition geometry, the geometry and orientation of the imaged anatomy, and other parameters may be evaluated to determine the best placement of the source 12 for the next projection. In addition, the amount of scattered radiation in the direction of the clinician may be taken into account. In addition, other clinically relevant information, such as synchronization with an electrocardiogram signal, i.e., prospective gating, auto-contrast injection device, catheter position, elapsed time since acquisition of the last X-ray image, or local information content in the image may be used in the determination of the time and position of a successive image acquisition. For example, feedback from the three-dimensional image reconstruction or analysis or from electromagnetic positioning sensors may be used to adaptively update the region of interest that is exposed, such as to track the tip of a catheter.

Similarly, timing and position information may be determined based on a pre-shot used to automatically establish the exposure parameters. Such a pre-shot may be particularly useful in determining the orientation of the initial images, if no other information is available. In addition, a video image, such as may be obtained by a video camera or other visual sensor may provide the position and orientation of the patient, a catheter, etc., which may be used to determine the timing and position of a successive fluoroscopic image. Based on the factors to be considered and the degree of control to be maintained by the operator, selection of position and time for a fluoroscopic image acquisition may be done automatically or semi-automatically, such as with computer generated and displayed prompts, and may utilize pre-set or interactive input by the operator.

In addition, as noted above, the imaging system 10 may be configured to utilize electromagnetic positioning signals, such as RF markers. One possible use of such signals, as noted above, may be to track invasive tools and/or instruments, such as catheters. For example, a set of fluoroscopic projection images may be initially acquired and one or more suitable three-dimensional images reconstructed from the projection images. The fluoroscopic and three-dimensional images may be correlated with an electromagnetic signal associated with a device, such as a catheter, at one position. To reduce the X-ray dose associated with the procedure, fluoroscopic imaging may be suspended while the catheter is moved. The position of the catheter, however, may be updated on the three-dimensional image based on the electro-magnetic signal. Fluoroscopic images may be acquired when desired to confirm the position information.

3. Image Resolution

In instances where the region of anatomic interest is relatively small or where sufficiently powerful computer and processor power is available, the full resolution of the detector 22 may be utilized for image acquisition. In other instances where less than the full detector resolution may be available or desired, the viewing area, the amount of image data, and/or the time required for three-dimensional reconstruction and viewing, may be reduced by a variety of means.

For example, full resolution projection images may be acquired by the detector 22 with the resulting acquired image data reduced or transformed to a lower resolution to facilitate faster processing downstream. In one example, the acquired projection images may be averaged or decimated to obtain lower resolution images which may be more quickly processed by subsequent reconstruction and viewing routines. Similarly, multi-resolution decomposition, wavelet decomposition, and other technique known to those of ordinary skill in the art may be used to generate projection images at resolutions lower than the full resolution of the detector 22. By means of this approach, acquisition is not performed faster, though subsequent processes, such as reconstruction and viewing, may be performed faster.

Alternatively, only that portion of the detector 22 corresponding to the region of interest may be read out, though it is read out at full resolution. Imaging resources are thereby focused on this region of interest. This approach allows faster projection image acquisition, as well as faster reconstruction and rendering. However, some proximate image data, which may be useful for providing anatomic context in the reconstructed images, may not be acquired. In this approach, and in other in which the portions of the detector 22 are differentially read out, the stream of radiation 16 may be differentially collimated with respect to the region of interest, thereby limiting X-ray dose and reducing scatter of the stream of radiation 16.

Similarly, the entire detector 22 may be read out, but that portion of the detector 22 corresponding to the region of interest detector 22 may be read out at full resolution while the remainder of the detector is read out at a lower resolution. Such an approach may maintain the highest possible image quality of the region of interest while still providing the context of nearby anatomy, albeit at a lower resolution. By means of this approach, projection image acquisition, reconstruction, and rendering times may be improved somewhat relative to full resolution acquisition over the entire detector. Subsequent reconstruction and rendering processes may be configured to correspond to the acquisition resolution of the projection images. Alternatively, the acquired projection images may be further reduced in size, as described above, to allow faster reconstruction and rendering processing. In addition, as noted above, the stream of radiation 16 may be differentially collimated, such that the acquisition rate of projection images for the region of interest may be higher than for the surrounding region.

It should be noted that the preceding approaches to acquisition resolution, frame timing and positioning, and scan trajectories may be combined with other known X-ray imaging and fluoroscopic acquisition methods for enhancement of the desired projection image data. For example, the present techniques may be used in conjunction with dual or multi-energy methods to enhance imaging of contrast agents, tissue immediately adjacent to contrast agents, and removal of bone structures in soft tissue images. Furthermore, image filtration and segmentation techniques that may be useful in the enhancement of projection image data may also be employed in conjunction with the present techniques.

4. Optional Pre-Scanning

Primary acquisition of the fluoroscopic image data, as described above, may be preceded by a pre-scan of the region of interest. Such a pre-scan may help improve the quality of the three-dimensional image subsequently generated. In addition, the pre-scan may further reduce the effect of overlying tissue in the resulting three-dimensional image. As one of ordinary skill in the art will appreciate, a fluoroscopic or record mode may be used for the pre-scan, as desired. The resulting three-dimensional image, discussed in greater detail below, may then be used during the clinical application (e.g. catheter insertion, bone repair, etc.) and a follow up three-dimensional image may be acquired afterward to confirm the success of the procedure.

II. Volume Reconstruction

Reconstruction of the acquired fluoroscopic image data into a three-dimensional image or volume may be accomplished by various processes. For example, the reconstruction may be accomplished by backprojection, filtered backprojection, algebraic reconstruction technique (ART), or any other reconstruction method known in the art. The projection images can be registered (or the acquisition geometry for each frame determined) from fiducial marks if available or anatomical markers present in the image. The implementation of the reconstruction technique may vary depending on the application and/or operator preferences.

For example, reconstruction of the image data may be incremental, i.e., an existing three-dimensional reconstructed dataset may be updated with information from one or more of the more recent acquired projection radiographs. Alternatively, the reconstruction may be based on a designated set of projection images, without using or updating information from a previous three-dimensional reconstruction. Furthermore, the projection images used for reconstruction or for updating the reconstruction may be selected based upon an external factor, such as a corresponding electrocardiogram signal, i.e., retrospective gating, acquisition geometry, timing, or other criteria, such as using the last N projection images for reconstruction.

Furthermore, the reconstruction process may differentially weight one or more projection images used in the reconstruction process. For example, differential weighting may be applied based upon the acquisition geometry of the acquired projection images. Similarly, projection image data may be weighted based on the respective timing of the acquired projection images, the time-delay since the image was acquired, a corresponding electrocardiogram signal, and so forth.

The reconstruction process may be differential in other respects. For example, the reconstruction process may be multi-resolution in time and/or space. For example, a region of interest may be reconstructed at a high resolution, while the surrounding volume may be reconstructed at a lower resolution sufficient to provide anatomical context. Similarly, the reconstruction of the region of interest may be computed or updated more often than the reconstruction of the surrounding volume.

In some contexts, the region of interest may be adaptively updated or modified based on information in the image or obtained from one or more positional sensors. In particular, in intraoperative contexts, all or part of an interventional device may determine the region of interest. For example, the region of interest may be determined by the location of a catheter tip, which may be tracked in the images or by a positional sensor associated with the catheter.

Similarly, in contexts in which the application pertains to the tracking of motion or the evolution of some process over time, the reconstruction process may comprise techniques that accentuate changes in the imaged volume. For example, the reconstruction process may reconstruct from difference images where projection images are acquired with the same relative source position. Alternatively, the reconstruction process may reproject the reconstructed volume according to the current system geometry and update the reconstructed volume in accordance with the difference image obtained at the current system geometry.

While the preceding discussion focuses on the reconstruction of a data set or volume, more than one reconstructed data set or volume may present at one time. Indeed, several reconstructed datasets can co-exist if desired. For example, reconstructed volumes corresponding to different "states" of the imaged anatomy may be concurrently maintained. An instance where this might be desired is in cardiac angiography, where it may be desirable to maintain a reconstructed volume for different cardiac states or phases, as determined from the electrocardiogram signal)

III. Volume Display

The reconstructed three-dimensional image may be displayed by a volume rendering technique on a display 42 and may be viewed from any direction of interest. In addition, the three-dimensional image may be displayed at full resolution or at a reduced resolution. As noted previously, the three-dimensional image may be viewed with or without the current fluoroscopic frame superimposed. If a fluoroscopic image is superimposed on the three-dimensional image, it will typically be displayed at the same resolution as the three-dimensional image to facilitate registration of the two images. The display 42 may be a multi-color display or a gray-scale display that allows the use of color or gray-scale intensity, respectively, to differentiate bone and soft tissue, or contrast agent and soft tissue, or the current fluoroscopic image from the volume rendering. Furthermore, the fluoroscopic image sequence may be displayed on a second display 42 at full resolution, if desired, without the superimposed three-dimensional structure, thereby assuring consistency with today's clinical practice.

To facilitate the perception of depth and/or motion, the volume rendering may be rotated or "tumbled" in a relatively small angle around the viewing direction defined by the most recent fluoroscopic image. In this way, the fluoroscopic image viewpoint, i.e., perspective, defines the viewing angle for three-dimensional rendering.

Alternatively, the three-dimensional rendering may be presented at any orientation. In this implementation, the viewpoint of the most recent fluoroscopic image may be indicated on the three-dimensional rendering, such as by a visual marker or axis. In particular, either the fluoroscopic image or the plane of the detector relative to the fluoroscopic image may be displayed to depict the orientation of the fluoroscopic image relative to the three-dimensional volume. The most recent fluoroscopic image may be superimposed on the three-dimensional image at a depth corresponding to the center of the volume, at the depth of a feature of interest, or at any other depth of interest.

Since the three-dimensional image may be viewed from any perspective, it may be useful to rotate the volume rendering to provide the best view for the present application. For example, during catheter insertion, the choice of which vessel to traverse at a bifurcation may be simplified by viewing the three-dimensional image perpendicular to the bifurcation. To facilitate viewing of the three-dimensional image at the desired perspectives, the operator may track the orientation of the rendering and reposition the image chain to facilitate viewing the anatomy and/or tools of interest.

The reconstructed and displayed three-dimensional image may provide various advantages compared to an imaging sequence comprised of fluoroscopic images alone. For example, since the three-dimensional image is reconstructed from projections acquired across a range of perspectives with respect to the anatomy of interest, the effect of overlying tissue on image clarity is significantly reduced. In addition, the three-dimensional image provides the anatomical context for each fluoroscopic view. Furthermore, the averaging inherent in the image reconstruction process may reduce the noise associated with the image and may enable dose reduction compared to standard fluoroscopic imaging with no three-dimensional image reconstruction.

The present technique may be applied in fluoroscopic systems used in a variety of applications such as radiography and fluoroscpcopy (r&f) systems, as well as vascular, surgical, and orthopedic imaging systems. While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for generating a three-dimensional image, comprising:
    acquiring two or more fluoroscopic projection images at different view angles relative to a region of interest, wherein the two or more fluoroscopic projection images are aligned using at least one of a fiducial marker or an anatomical structure; and
    reconstructing at least one three-dimensional image from the two or more fluoroscopic projection images.

2. The method, as recited in claim 1, wherein the step of acquiring the two or more fluoroscopic projection images comprises:
    moving at least a source in a trajectory relative to the region of interest; and
    emitting X-rays from the source at different locations on the trajectory such that the X-rays traverse the region of interest and impact a detector.

3. The method, as recited in claim 2, wherein the trajectory comprises a one-dimensional spatial trajectory, a two-dimensional spatial trajectory, or a three-dimensional spatial trajectory.

4. The method, as recited in claim 1, wherein the step of acquiring the two or more fluoroscopic projection images comprises:

obtaining position information about at least one of a source or a detector from an electro-magnetic signal.

5. The method, as recited in claim 1, wherein the step of acquiring the two or more fluoroscopic projection images comprises:
determining at least one of a time or a position for the acquisition of a fluoroscopic projection image to obtain at least one of a desired depth resolution, a suppression of overlying tissue, a reduction in image artifacts, an improvement in signal to noise, a desired acquisition geometry arid or a desired orientation of a structure in the region of interest.

6. The method, as recited in claim 1, wherein the step of acquiring the two or more fluoroscopic projection images comprises:
determining at least one of a time or a position for the acquisition of a fluoroscopic projection image based on at least one of an electrocardiogram signal, an automated contrast agent injection, elapsed image acquisition time, feedback based on a displayed three-dimensional image, a positional sensor associated with an invasive device, a pre-shot for establishing exposure parameters, or a video image.

7. The method, as recited in claim 1, wherein the step of acquiring the two or more fluoroscopic projection images comprises:
determining at least one of a time or a position for the acquisition of a fluoroscopic projection image automatically.

8. The method, as recited in claim 1, wherein the step of acquiring the two or more fluoroscopic projection images comprises:
determining at least one of a time and or a position for the acquisition of a fluoroscopic projection image semi-automatically.

9. The method, as recited in claim 1, comprising:
correlating at least one of a fluoroscopic projection image or a three-dimensional image with an electro-magnetic position signal associated with an invasive device.

10. The method' as recited in claim 1, comprising:
converting the two or more fluoroscopic projection images to respective lower resolution images.

11. The method, as recited in claim 1, wherein the step of acquiring the two or more fluoroscopic projection images comprises:
reading out only a portion of a detector; wherein the portion corresponds to the region of interest.

12. The method, as recited in claim 1, wherein the step of acquiring the two or more fluoroscopic projection images comprises:
reading out a first portion of a detector associated with the region of interest at a first resolution; and
reading out a second portion of a detector not associated with the region of interest at a second resolution, wherein the second resolution is lower than the first resolution.

13. The method, as recited in claim 1, comprising:
pre-scanning the region of interest.

14. The method, as recited in claim 1, wherein the step of reconstructing at least one three-dimensional image comprises:
registering the two or more fluoroscopic projection images based on at least one of a fiducial mark or an anatomical marker.

15. The method, as recited in claim 1, wherein the step of reconstructing at least one three-dimensional image comprises:
updating an existing three-dimensional image using at least one recent fluoroscopic projection image.

16. The method, as recited in claim 1, wherein the step of reconstructing at least one three-dimensional image comprises:
selecting two or more fluoroscopic projection images for reconstruction based on at least one of an electrocardiogram signal, an acquisition geometry, or a configured number of projections to be used for reconstruction into a three-dimensional image.

17. The method, as recited in claim 1, wherein the step of reconstructing at least one three-dimensional image comprises:
weighting one or more fluoroscopic projection images used in the reconstruction process differentially.

18. The method as recited in claim 17, wherein the weighting is applied based on at least one of an acquisition geometry, a time of acquisition, an elapsed time, or an electrocardiogram signal.

19. The method, as recited in claim 1, wherein the step of reconstructing at least one three-dimensional image comprises:
reconstructing the region of interest at a first resolution; and
reconstructing a volume outside the region of interest at a second resolution, wherein the second resolution is less than the first resolution.

20. The method, as recited in claim 1, wherein the step of reconstructing at least one three-dimensional image comprises:
reconstructing the region of interest more frequently than a volume outside the region of interest.

21. The method, as recited in claim 1, wherein the two or more fluoroscopic projection images comprise difference images.

22. The method, as recited in claim 1, comprising:
rendering the at least one three-dimensional image.

23. The method, as recited in claim 22, comprising:
superimposing a current fluoroscopic projection image on the rendered three-dimensional image.

24. The method, as recited in claim 22, comprising:
displaying a visual indicator with the rendered three-dimensional image to indicate a viewpoint of the most recent fluoroscopic projection image.

25. One or more computer readable media encoded with a computer program for generating a three-dimensional image, the computer program comprising:
a routine for acquiring two or more fluoroscopic projection images at different view angles relative to a region of interest, wherein the two or more fluoroscopic projection images are aligned using at least one of a fiducial marker or an anatomical structure; and
a routine for reconstructing at least one three-dimensional image from the two or more fluoroscopic projection images.

26. The one or more computer readable media, as recited in claim 25, wherein the routine for acquiring moves at least a source in a trajectory relative to the region of interest and causes the source to emit X-rays at different locations on the trajectory such that the X-rays traverse the region of interest and impact a detector.

27. The one or more computer readable media, as recited in claim 26, wherein the trajectory comprises a one-dimensional spatial trajectory, a two-dimensional spatial trajectory, or a three-dimensional spatial trajectory.

28. The one or more computer readable media, as recited in claim 25, wherein the routine for acquiring obtains position information about at least one of a source or a detector from an electro-magnetic signal.

29. The one or more computer readable media, as recited in claim 25, wherein the routine for acquiring determines at least one of a time and or a position for the acquisition of a fluoroscopic projection image to obtain at least one of a desired depth resolution, a suppression of overlying tissue, a reduction in image artifacts, an improvement in signal to noise, a desired acquisition geometry, or a desired orientation of a structure in the region of interest.

30. The one or more computer readable media, as recited in claim 25, wherein the routine for acquiring determines at least one of a time or a position for the acquisition of a fluoroscopic projection image based on at least one of an electrocardiogram signal, an automated contrast agent injection, elapsed image acquisition time, feedback based on a displayed three-dimensional image, a positional sensor associated with an invasive device, a pre-shot for establishing exposure parameters, or a video image.

31. The one or more computer readable media, as recited in claim 25, comprising:
   a routine for correlating at least one of a fluoroscopic projection image or a three-dimensional image with an electro-magnetic position signal associated with an invasive device.

32. The one or more computer readable media, as recited in claim 25, comprising:
   a routine for converting the two or more fluoroscopic projection images to respective lower resolution images.

33. The one or more computer readable media, as recited in claim 25, wherein the routine for acquiring reads out only a portion of a detector; wherein the portion corresponds to the region of interest.

34. The one or more computer readable media, as recited in claim 25, wherein the routine for acquiring reads out a portion of a detector associated with the region of interest at a first resolution and reads out a portion of a detector not associated with the region of interest at a second resolution, wherein the second resolution is lower than the first resolution.

35. The one or more computer readable media, as recited in claim 25, comprising:
   a routine for pre-scanning the region of interest.

36. The one or more computer readable media, as recited in claim 25, wherein the routine for reconstructing registers the two or more fluoroscopic projection images based on at least one of a fiducial mark or an anatomical marker.

37. The one or more computer readable media, as recited in claim 25, wherein the routine for reconstructing updates an existing three-dimensional image using at least one recent fluoroscopic projection image.

38. The one or more computer readable media, as recited in claim 25, wherein the routine for reconstructing selects two or more fluoroscopic projection images for reconstruction based on at least one of an electrocardiogram signal, an acquisition geometry, or a configured number of projections to be used for reconstruction into a three-dimensional image.

39. The one or more computer readable media, as recited in claim 25, wherein the routine for reconstructing weights one or more fluoroscopic projection images used in the reconstruction process differentially.

40. The one or more computer readable media, as recited in claim 39, wherein the routine for reconstructing weights the one or more fluoroscopic projection images based on at least one of an acquisition geometry, a time of acquisition, an elapsed time or an electrocardiogram signal.

41. The one or more computer readable media, as recited in claim 25, wherein the routine for reconstructing reconstructs the region of interest at a first resolution and reconstructs a volume outside the region of interest at a second resolution, wherein the second resolution is less than the first resolution.

42. The one or more computer readable media, as recited in claim 25, wherein the routine for reconstructing reconstructs the region of interest more frequently than a volume outside the region of interest.

43. The one or more computer readable media, as recited in claim 25, wherein the two or more fluoroscopic projection images comprise difference images.

44. The one or more computer readable media, as recited in claim 25, comprising:
   a routine for rendering the at least one three-dimensional image.

45. The one or more computer readable media, as recited in claim 44, comprising:
   a routine for superimposing a current fluoroscopic projection image on the rendered three-dimensional image.

46. The one or more computer readable media, as recited in claim 44, comprising:
   a routine for displaying a visual indicator with the rendered three-dimensional image to indicate a viewpoint of the most recent fluoroscopic projection image.

47. A fluoroscopic imaging system, comprising:
   means for acquiring two or more fluoroscopic projection images at different view angles relative to a region of interest, wherein the two or more of the fluoroscopic projection images are aligned using at least one of a fiducial marker or an anatomical structure; and
   means for reconstructing at least one three-dimensional image from the two or more fluoroscopic projection images.

48. A fluoroscopic imaging system, comprising:
   an X-ray source configured to emit a stream of radiation through a volume of interest from different positions relative to a region of interest;
   a detector comprising a plurality of detector elements, wherein each detector element generates one or more signals in response to respective streams of radiation;
   a system controller configured to control the X-ray source and to acquire the one or more signals from the plurality of detector elements;
   a computer system configured to generate two or more fluoroscopic projection images of the region of interest from different perspectives from the one or more signals, wherein the two or more fluoroscopic projection images are aligned using at least one of a fiducial marker or an anatomical structure, and to reconstruct at least one three-dimensional image from the two or more fluoroscopic projection images; and
   an operator workstation configured to display at least one three-dimensional image.

49. The fluoroscopic imaging system, as recited in claim 48, wherein the X-ray source is configured to move in at least one of a one-dimensional spatial trajectory, a two-dimensional spatial trajectory, or a three-dimensional spatial trajectory.

50. The fluoroscopic imaging system, as recited in claim 48, wherein at least one of the X-ray source or the detector comprises a position indicator.

51. The fluoroscopic imaging system, as recited in claim 50, wherein the position indicator generates an electromagnetic position signal.

52. The fluoroscopic imaging system, as recited in claim 48, wherein the system controller is configured to read out only a portion of the detector, wherein the portion corresponds to the region of interest.

53. The fluoroscopic imaging system, as recited in claim 48, wherein the system controller is configured to read out a first portion of the detector associated with the region of interest at a first resolution and to read out a second portion of a detector not associated with the region of interest at a second resolution, wherein the second resolution is lower than the first resolution.

54. The fluoroscopic imaging system, as recited in claim 48, wherein the computer system is configured to pre-scan the region of interest.

55. The fluoroscopic imaging system, as recited in claim 48, wherein the two or more fluoroscopic projection images comprise difference images.

56. The fluoroscopic imaging system, as recited in claim 48, wherein the operator workstation is configured to superimpose a current fluoroscopic projection image on a rendered three-dimensional image.

* * * * *